United States Patent
Horrigan

(10) Patent No.: US 10,159,549 B1
(45) Date of Patent: Dec. 25, 2018

(54) PET BANDAGE FEATURING RESISTANCE AGAINST CHEWING OR TEARING BY PET

(71) Applicant: Richard P Horrigan, Roxbury, CT (US)

(72) Inventor: Richard P Horrigan, Roxbury, CT (US)

(*) Notice: Subject to any disclaimer, the term of this patent is extended or adjusted under 35 U.S.C. 154(b) by 0 days.

(21) Appl. No.: 15/732,526

(22) Filed: Nov. 22, 2017

Related U.S. Application Data

(60) Provisional application No. 62/497,608, filed on Nov. 25, 2016.

(51) Int. Cl.
*A61D 9/00* (2006.01)
*A01K 13/00* (2006.01)
*A61F 13/00* (2006.01)

(52) U.S. Cl.
CPC .............. *A61D 9/00* (2013.01); *A01K 13/006* (2013.01); *A61F 2013/00251* (2013.01)

(58) Field of Classification Search
CPC ...... A61D 9/00; A01K 13/006; A01K 13/007; A01K 27/001; A61F 13/00029; A61F 2013/00165; A61F 2013/00246; A61F 2013/00255; A61F 13/00089; A61F 2013/00251; A61F 2013/00089
USPC ................. 602/42, 58, 59; 128/888
See application file for complete search history.

(56) References Cited

U.S. PATENT DOCUMENTS

| | | | | |
|---|---|---|---|---|
| 697,637 | A * | 4/1902 | Lee | A61F 15/008 128/888 |
| 2,367,690 | A * | 1/1945 | Purdy | A61F 15/006 128/888 |
| 2,785,677 | A * | 3/1957 | Stumpf | A61F 15/008 128/888 |
| 4,212,296 | A * | 7/1980 | Scheer | A61F 13/0203 128/888 |
| 4,404,789 | A * | 9/1983 | Denning | A01K 13/006 2/15 |
| 4,667,666 | A * | 5/1987 | Fryslie | A61F 13/0226 128/888 |
| 4,709,695 | A * | 12/1987 | Kohn | A61F 9/04 128/858 |
| 5,086,763 | A * | 2/1992 | Hathman | A61F 13/0246 128/887 |
| 5,144,958 | A * | 9/1992 | Krueger | A61F 15/008 128/888 |
| 5,259,835 | A * | 11/1993 | Clark | A61F 13/0246 602/48 |
| 5,405,312 | A * | 4/1995 | Jacobs | A41D 13/0568 128/892 |
| 5,562,107 | A * | 10/1996 | Lavender | A61F 13/0269 128/888 |

(Continued)

*Primary Examiner* — Magdalena Topolski
(74) *Attorney, Agent, or Firm* — K. Gibner Lehmann

(57) ABSTRACT

A bandage for protecting a wound site in the extremity of an animal such as a dog or pet, has a body in the form of an inverted cup with a transverse wall and one or more access openings therein, a lip on the cup to fit against the animal's fur around the wound site, and a cover piece to enable selective covering of the access opening. The cup has a roughened exterior surface texture that is extremely irritating to the animal's tongue or lip, wherein the animal is discouraged from continuous licking and/or chewing on the body, and thereby inadvertently dislodging it from the wound site.

1 Claim, 5 Drawing Sheets

(56) References Cited

U.S. PATENT DOCUMENTS

| | | | | |
|---|---|---|---|---|
| 5,702,356 A * | 12/1997 | Hathman | A61F 13/0206 | 128/888 |
| 5,954,679 A * | 9/1999 | Baranitsky | A61F 13/0203 | 128/888 |
| 6,013,097 A * | 1/2000 | Augustine | A61F 7/007 | 602/14 |
| 6,107,536 A * | 8/2000 | Dadinis | A61F 15/008 | 128/889 |
| 6,274,787 B1 * | 8/2001 | Downing | A61F 15/008 | 602/14 |
| 6,586,651 B2 * | 7/2003 | Sullivan | A61F 13/0203 | 602/41 |
| 7,396,975 B2 * | 7/2008 | Sigurjonsson | A61F 13/0203 | 128/888 |
| 8,011,328 B2 * | 9/2011 | Pitzen | A61D 9/00 | 119/859 |
| 8,578,891 B2 * | 11/2013 | Vickery | A01K 13/006 | 119/850 |
| 2002/0026124 A1 * | 2/2002 | Whitaker | A01K 11/00 | 600/551 |
| 2002/0124812 A1 * | 9/2002 | Sjolin | A61D 9/00 | 119/850 |
| 2003/0009122 A1 * | 1/2003 | Veras | A61F 15/008 | 602/42 |
| 2005/0054965 A1 * | 3/2005 | Kirkis | A61F 13/023 | 602/42 |
| 2005/0107732 A1 * | 5/2005 | Boyde | A61F 15/008 | 602/41 |
| 2007/0062462 A1 * | 3/2007 | McGuire | A01K 13/006 | 119/850 |
| 2007/0142757 A1 * | 6/2007 | Aali | A61F 13/00068 | 602/2 |
| 2009/0105625 A1 * | 4/2009 | Kohner | A61F 13/068 | 602/54 |
| 2013/0220347 A1 * | 8/2013 | Al Otaibi | A61F 15/004 | 128/888 |
| 2014/0358058 A1 * | 12/2014 | Nelson | A61F 13/00063 | 602/48 |
| 2017/0202711 A1 * | 7/2017 | Cernasov | A61F 13/00021 | |
| 2017/0296391 A1 * | 10/2017 | Kendall | A61F 13/00059 | |

\* cited by examiner

PET BANDAGE FEATURING RESISTANCE AGAINST CHEWING OR TEARING BY PET

CROSS REFERENCE TO RELATED APPLICATION

The present Utility Patent application claims priority of my Provisional application U.S. Ser. No. 62/497,608 filed Nov. 25, 2016, and having common ownership therewith.

FIELD OF THE INVENTION

The present invention relates generally to bandages for pets, particularly the legs of a dog, for covering wounds which periodically occur and which persist due to the animal's tendency to lick the wound, and thereby interfere with natural healing thereof.

BACKGROUND OF THE INVENTION AND SAMPLING OF PRIOR ART

In the case of pets such as dogs, even minor irritation of their skin can begin a degenerative series of steps leading to development of what is known in the veterinary profession as a "hot spot". In particular, the technical name is "acute moist dermatitis". The onset of inflammation happens quickly, and the dog's natural instinct is to begin licking or chewing at the affected area; this in turn compounds the natural healing process and can lead to a chronic infection that can be most difficult to treat.

A rather old solution to the problem of controlling the pet's licking/chewing tendency is the use of an oversized conical bonnet that is fitted around the animal's neck and thereby restricts movement of his jaw (and tongue, teeth, etc.) This bars his access to the affected area. However such bonnets are clumsy at best, and with larger animals, an "oversized" bonnet tends to bump into indoor furnishings and/or other objects in the area where the animal roams. With multiple dogs wearing bonnets, their random and aggressive movements can wreck the contents of a home in short order.

Other proposals include use of a bitter tasting liquid of a non-toxic variety, applied to the area surrounding the existing wound. The substance is purposely made to be so unpalatable to taste, that the dog will avoid licking at the location of the applied substance.

A commercially available wrap material is currently being marketed under the name, "PowerFlex No Chew Bandage" by a company operating under the name Dover Saddlery, of Littleton Mass. The Bandage is sold as a roll, off which a desired length can be selected and separated from the roll by simple tearing. This length can then be taped around a gauze or other type dressing. The roughness of the PowerfFlex purportedly tends to irritate the nose or lips of the animal, to the end that the wound beneath the dressing remains essentially undisturbed while it is allowed to heal naturally. Optional ointment can also be applied to the wound prior to use of the PowerFlex wrap.

SUMMARY OF THE INVENTION

While some of the devices above noted have achieved a degree of success, there has not, to date, been an effective bandage arrangement that would function acceptably to keep an animal such as a pet, from chewing or biting the affected area, and thereby defeating natural healing.

The present invention particularly addresses this problem as outlined above, and thus obviates some of the drawbacks and disadvantages of conventional bite-resistant bandages and/or dressings made specifically for animals.

The invention is thereby considered to have at least some of the following objects:

To provide a novel and improved bandage for covering the site of a wound on an extremity of a dog or other pet.

To provide an improved bandage in accordance with the foregoing, which is easy to use, and which can be fabricated at low cost.

To provide an improved bandage as above characterized which can be readily changed, and replaced by a fresh bandage following a desired period of use.

To provide an improved bandage of the kind indicated, which features selective modes of healing, namely a fully covered condition, or an open condition which facilitates application of medicament, or which encourages circulation of air to a wound site.

The objects are accomplished by a bandage for protecting a wound site in the extremity of an animal such as a dog or pet, including in combination a body comprising an inverted cup with a transverse bottom wall and an open top having a peripheral lip, said peripheral lip being adapted to engage the area around the wound site, when the bandage is applied, a securement strap connected with said body, said strap having at least one free end for wrapping around the animal's extremity and securing the body thereto, said transverse bottom wall having an access opening to enable communication between the interior of the cup and the exterior of the cup, said access opening permitting manual, selective application of topical dressing to the wound site, or for promoting circulating air through the transverse wall and onto the wound site, or alternately for blocking entry of undesirable contaminants to the wound site through the access opening, a cover piece to be selectively, manually applied to said transverse wall, covering the access opening and thereby isolating the interior of the cup and the corresponding wound site from the exterior of the cup, and said cup having a roughened surface texture that is extremely irritating to the animal's tongue or lip, thereby discouraging it from licking the cup and/or chewing on it and thereby dislodging it from the wound site.

Other features and advantages will hereinafter appear.

BRIEF DESCRIPTION OF THE DRAWINGS

In the accompanying drawings illustrating a preferred embodiment of the invention.

Figure 1:
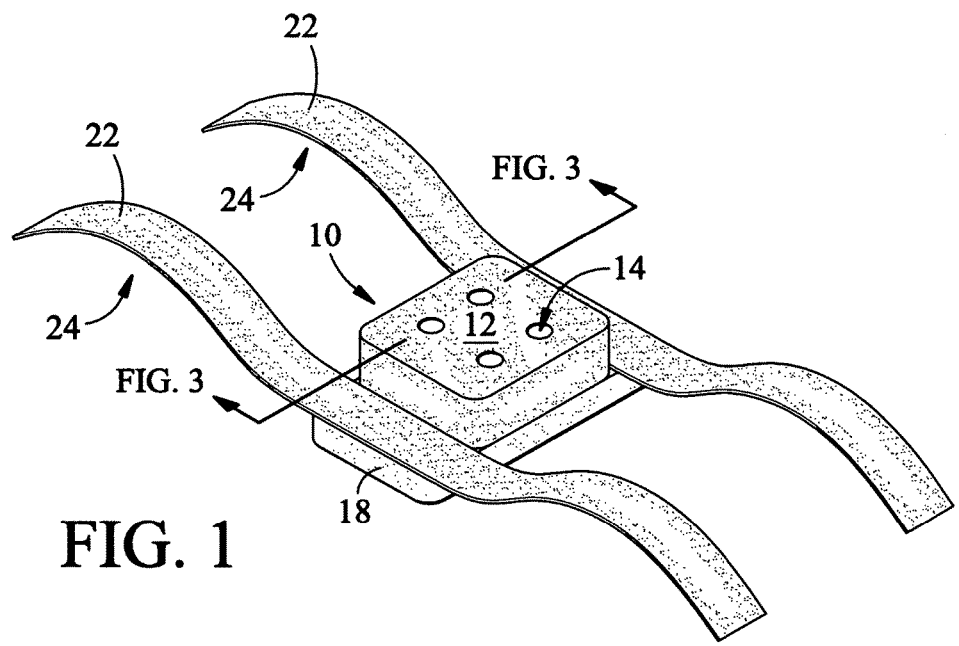
FIG. 1 is perspective top view of the improved bandage of the present invention.

DESCRIPTION OF THE PREFERRED EMBODIMENT, AND BEST MODES FOR CARRYING OUT THE INVENTION AS OF THE INSTANT FILING DATE

Referring now to FIGS. 1-4 of the drawings, there is illustrated a bandage for covering a wound site or sore in the extremity of a pet, in the present case, a dog, with an objective to assist in healing of the wound, and also avoiding contamination thereof resulting from the tendency for the dog to disturb the bandage during its useful life.

There is provided an inverted cup 10 having a bottom transverse wall 12 with one or more access openings 14, and an open lip with a flange 18 extending outwardly from at least part of the lip.

By the invention the exterior surfaces of substantially all of the cup 10 are characterized by a roughened exterior surface configuration which operates to discourage the animal from licking/chewing the bandage after it has been applied. In this connection, substantially all exterior surfaces of the cup 10 are fitted with Velcro® brand hook loop fastener 20, with a rough face of the Velcro® brand hook loop fastener facing outwardly. As is known, Velcro® brand hook loop fastener has a loop configuration on one portion, whereas another portion has a hook configuration. In the present instance, the covering 20 of the cup 10 and flange 18 utilizes the hook configuration of the Velcro® brand hook loop fastener.

Figure 2:
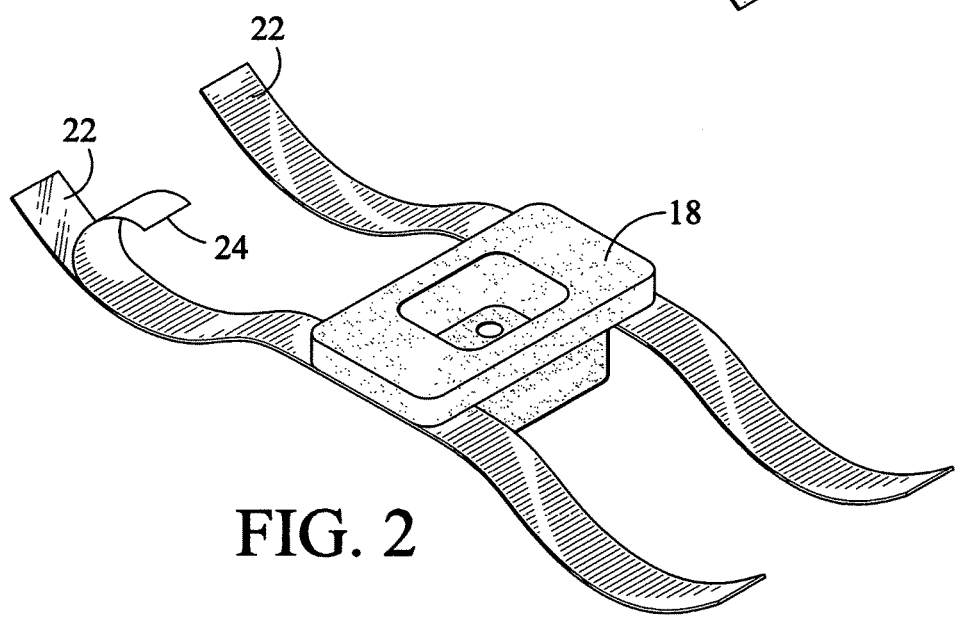
FIG. 2 is a perspective bottom view of the bandage.
Figure 3:
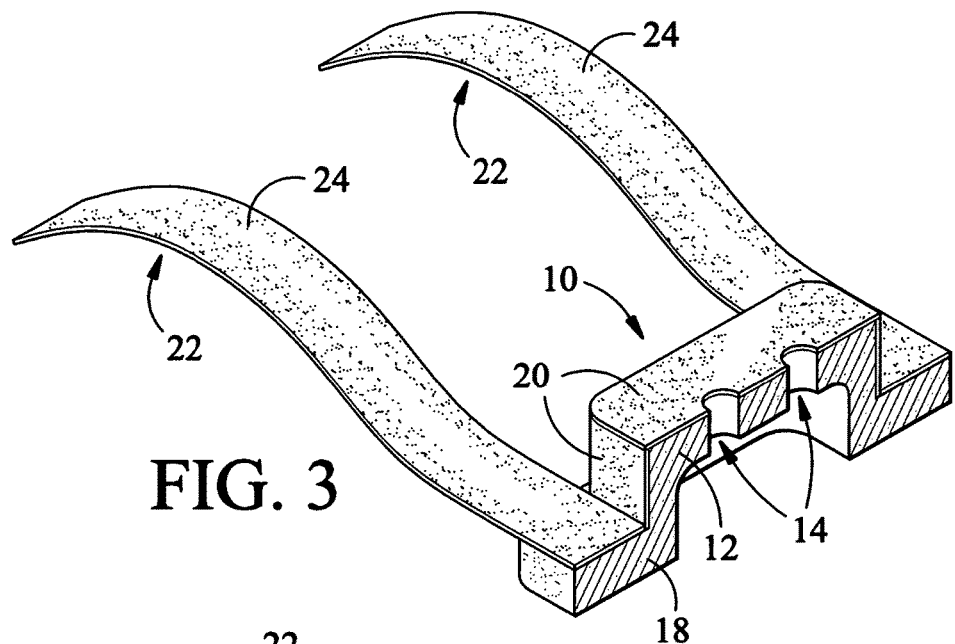
FIG. 3 is a vertical transverse section of the bandage taken on the line 3-3 of FIG. 1.

The cup is secured in place by one or more straps 22, as shown. The opposite ends of each strap can be tied around the animal's extremity, or alternately can be fabricated with an adhesive surface featuring a peel-off strip 24, for making the attachment. Such peel-off strips are shown in FIG. 2.

Figure 4:
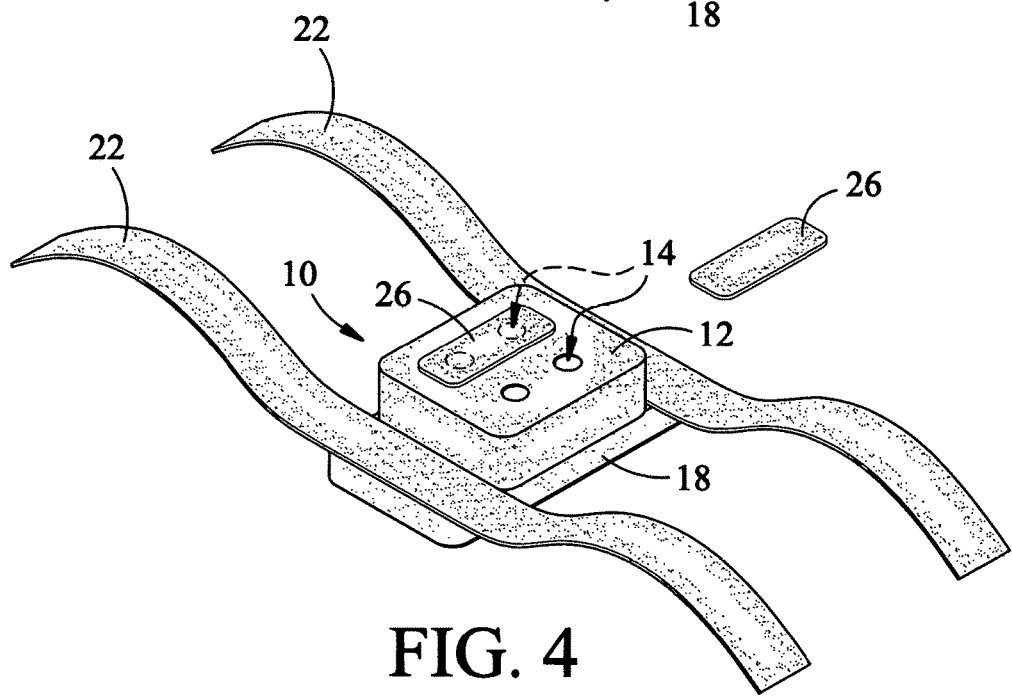
FIG. 4 is a view like FIG. 1, and illustrating detachable cover pieces for use with the bandage.

Cooperable with the access openings 14 are removable cover pieces 26, one being shown in perspective in FIG. 4. The cover pieces can be made from the same Velcro material, using two layers joined back to back, such that one face presents the rough, loop characteristic, and the opposite face presents the smooth, fabric characteristic. By this arrangement, each cover piece, when in position over one or two access openings, presents a roughened surface that in effect constitutes a continuation of the surface of the cup 10, whereas the other side presents the fabric-face that enables the cover piece 26 to adhere to the outside surface of the cup 10, when the cover piece is in a storage position. Because of the roughened surface of the cover piece 26, it similarly tends to resist incidental removal by the animal if he attempts to lick or chew on the piece.

The disclosed arrangement features flexibility to the bandage depending on what type of healing is being sought. In the drawings, a total of four access openings is shown, and in FIG. 4, two cover pieces 26 are illustrated, on in position and one removed and shown separated from the cup transverse wall 12. By utilizing two cover pieces and concealing all four access openings 14, the wound site is effectively isolated from the exterior, to the end that contaminants and/or undesirable debris be prevented from entering the wound site within the cup and its flange.

On the other hand, one or two of the access openings 14 can be left uncovered, as indicated in FIG. 4. This will allow limited circulation of air into the cup interior. Alternately, with the access pieces removed, appropriate medication (not shown) can be introduced into the wound site by a suitable wand, and the cover pieces either installed in position on the access opening, or else removed therefrom if air circulation is desired.

Figure 6:
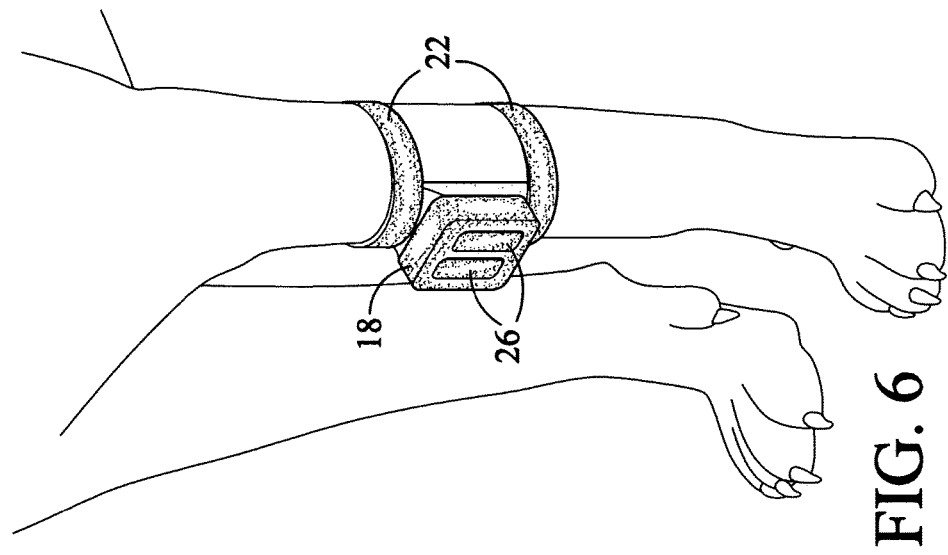
FIG. 6 is a perspective view of the bandage in operative position on the leg of the animal.
Figure 5:
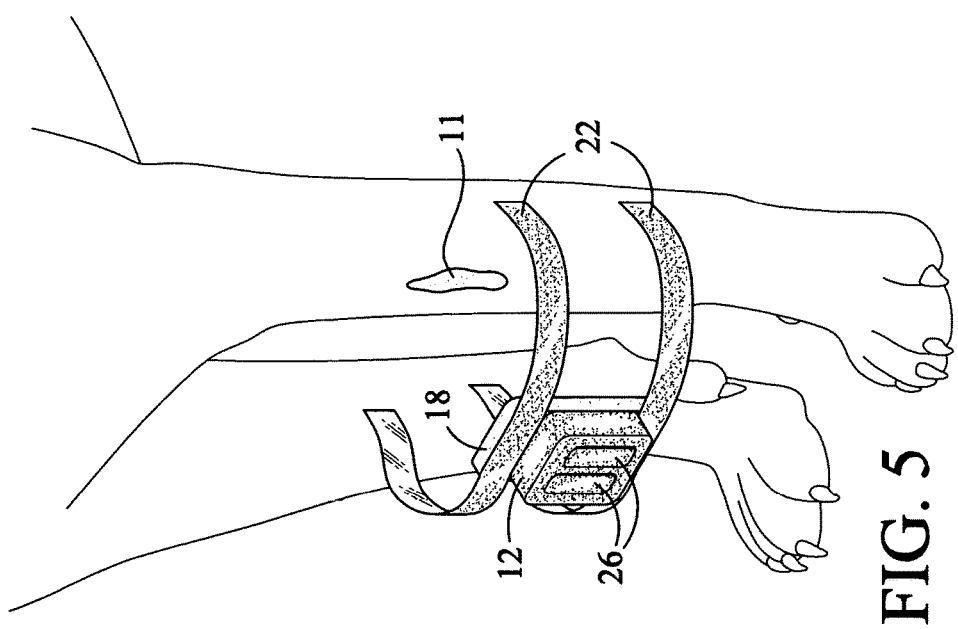
FIG. 5 is a perspective view of the bandage of the present invention in the position it would appear, as it is about to be applied to one leg of an animal.

FIGS. 5 and 6 show the method of application of the bandage of the invention, to the leg of a dog. As noted above, the bandage is intended to be a throwaway item, and it can be readily removed and a fresh unit substituted therefor, as can be readily understood by one of ordinary skill in the art.

As an alternative to the use of Velcro® brand hook loop fastener for the surface covering of the cup, it will also be understood that a different kind of roughened surface can be utilized, such as a modified strip of sandpaper with suitable means for fastening it in place. While this has not been tested in trials, it is contemplated that this broad concept of providing a roughened surface is to be considered part of the present disclosure.

Figure 7:
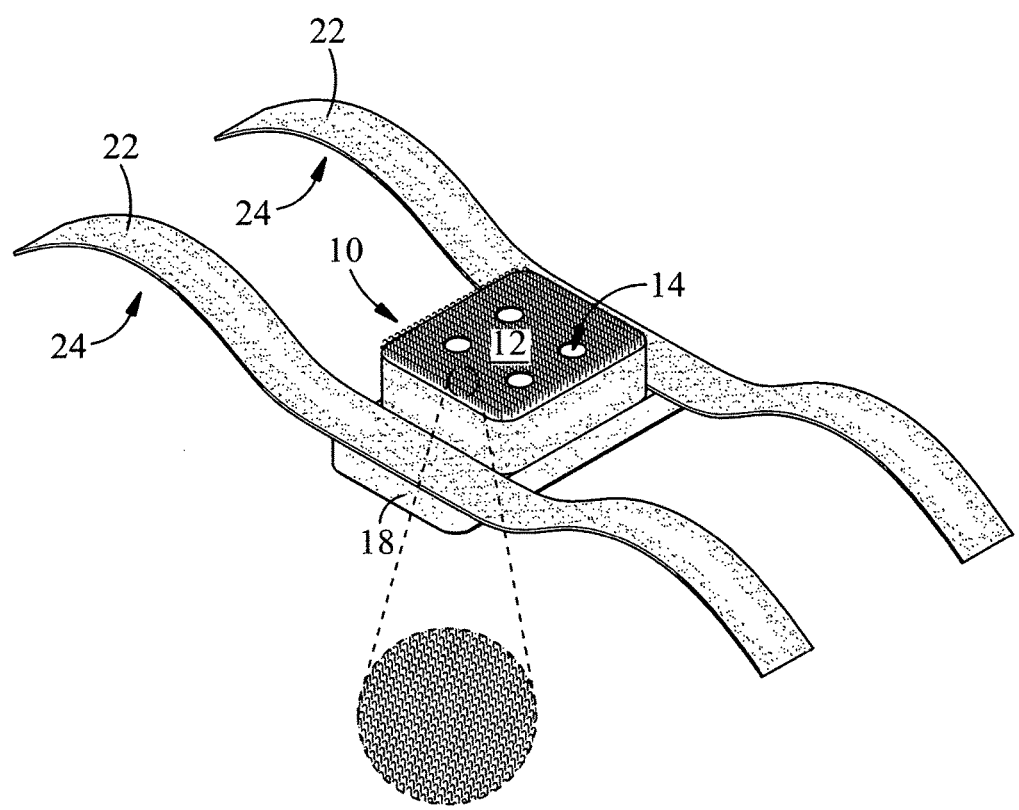
FIG. 7 is an exploded view of the surface area represented by the small circle in the body of the bandage, showing an enlargement of an array of Velcro hooks as preferably used in the device, for resistance against an animal or pet, chewing or tearing on the bandage.
Figure 8:
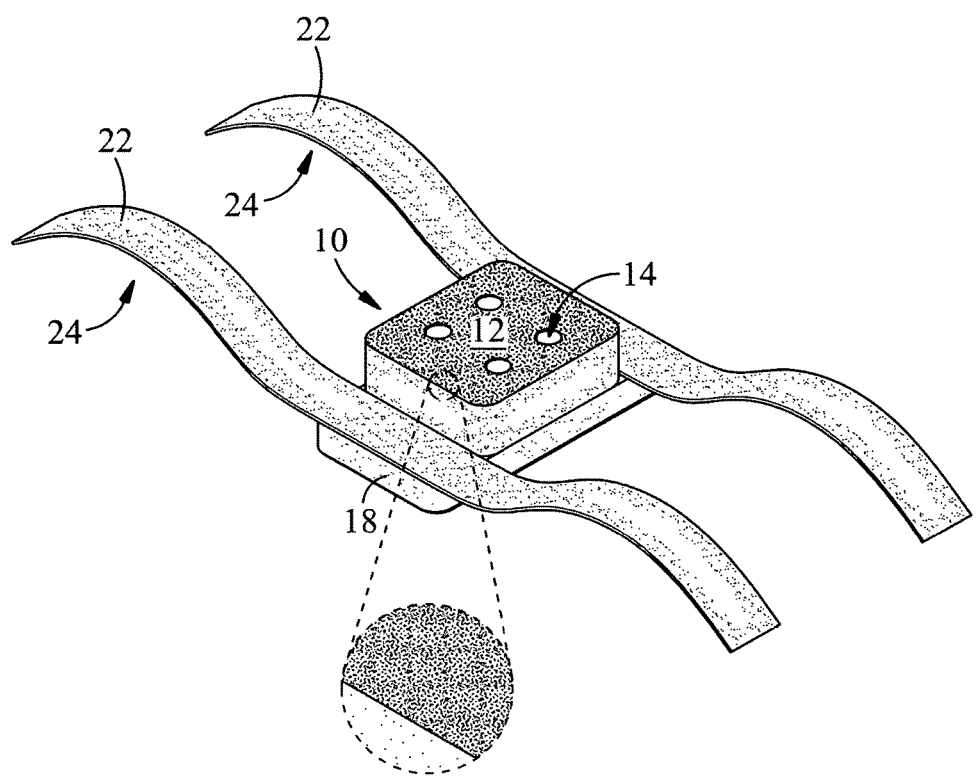
FIG. 8 is view like FIG. 7, except showing the use of sandpaper adhered to the bandage surface for the same reason as given in the previous paragraph.

In FIG. 7, there is shown an exploded view of the surface of a bandage constructed in accordance with the present invention. In particular, the use of an array or plurality of hooks of Velcro type material is seen, as constituting a main embodiment of the invention.

From the above it can be seen that I have provided a novel and improved bandage which is simple in its structure, resistant to chewing/licking by the animal, and capable of easy attachment and removal at the desired time intervals. The bandage thus constitutes a distinct advance and improvement in the field of animal care and/or veterinary practice.

The present invention may be embodied in other specific forms without departing from the spirit of any of the essential attributes thereof; therefore, the illustrated embodiments should be considered in all respects as illustrative and not restrictive, reference being made to the appended claims and to the foregoing description, to indicate the scope of the invention.

Variations and modifications are possible without departing from the spirit of the invention.

LIST OF REFERENCE NUMERALS

10 cup
11 wound site
12 transverse wall
14 access opening
18 flange
20 Velcro® brand, loop and fastener layer
22 straps
24 adhesive peel off strips
26 cover piece The embodiments of the invention in which an exclusive property or privilege is claimed are defined as follows:

1. A bandage for protecting a wound site of one of a dog and pet, comprising in combination:
   a) a body comprising an inverted cup with a transverse bottom wall and an open top having a peripheral lip, to overlie the wound site, when the bandage is applied,
   b) a securement strap connected with said body, said strap having at least one free end securing the body to the said one of a dog and pet,
   c) said transverse bottom wall having an access opening to enable manual, selective application of topical dressing to the wound site, or for promoting circulating air through the transverse wall and onto the wound site,
   d) a cover piece to be selectively, manually applied to said transverse wall, covering the access opening and thereby isolating the wound, and blocking entry of undesirable contaminants to the wound site through the access opening, e) said cup having, on substantially its entire exterior surface, a roughened surface texture that is extremely irritating to the dog or pet's tongue or lip, thereby discouraging it from one of licking the cup and chewing on it, and consequently dislodging it from the wound site, f) said roughened surface texture comprising a hook loop fastener, with its hooks facing outwardly and its loops facing inwardly on the cup, and wherein g) said cover piece comprising roughened surfaces on top and bottom sides thereof, wherein the roughened surfaces comprise hook loop fasteners and wherein the bottom side roughed surface of the cover piece is cooperable with the hook loop fastener of said roughened surface texture of the cup, to enable selective retention of said cover piece between being over said access opening and remote from said access opening, in the latter case being adapted for storage of said cover piece, and such that in either orientation a large portion of the roughened surface texture of the bottom wall of the cup remains exposed and such that the top roughened surface of cover piece is exposed to the dog or pet.

* * * * *